(12) United States Patent
Nishihara et al.

(10) Patent No.: US 8,309,743 B2
(45) Date of Patent: Nov. 13, 2012

(54) COMPOUND COMPRISING TRIARYLAMINE MOIETIES AND A CONDENSED RING MOIETY, AND THE PRODUCTION METHOD THEREOF

(75) Inventors: Hiroshi Nishihara, Bunkyo-ku (JP); Mikihiro Hayashi, Bunkyo-ku (JP); Fumiyuki Toshimitsu, Bunkyo-ku (JP)

(73) Assignee: The University of Tokyo, Tokyo (JP)

( * ) Notice: Subject to any disclaimer, the term of this patent is extended or adjusted under 35 U.S.C. 154(b) by 160 days.

(21) Appl. No.: 12/723,293

(22) Filed: Mar. 12, 2010

(65) Prior Publication Data

US 2011/0077416 A1   Mar. 31, 2011

(30) Foreign Application Priority Data

Sep. 7, 2009   (JP) .................. 2009-205510

(51) Int. Cl.
*C07D 311/02* (2006.01)
*C07D 307/00* (2006.01)
(52) U.S. Cl. ...................... 549/283; 549/320
(58) Field of Classification Search .......... 549/283, 549/320
See application file for complete search history.

(56) References Cited

FOREIGN PATENT DOCUMENTS

WO   2009/098792 A1   8/2009

OTHER PUBLICATIONS

Rossi et al. Tetrahedron, 1998, 54, 135-136.*
Sakamoto, R.; Kume, S.; Nishihara, H. Chem.—Eur. J. 2008, 14, 6978-6986.*
Uchiyama et al. Organic Letters, 2006, 8(34), 5517-5520.*
Letsinger et al. Journal of American Chemical Society, 1965, 87(4), 742-749.*
Dorwald F. A. Side Reactions in Organic Synthesis, 2005, Wiley: VCH, Weinheim p. IX of Preface p. 1-15.*
Rossi, R., et al., "Studies on the Transition Metal-Catalyzed Synthesis of Variously Substituted(E)-3[1-(Aryl)methylidene]- and (E)-3-(1-Alkylidene)-3H-furan-2-ones," Tetrahedron 54(1-2):135-156, Jan. 1, 1998.
Sakamoto, R., et al., "Visible-Light Photochromism of Triarylamine- or Ferrocene-Bound Diethynylethenes that Switches Electronic Communication Between Redox Sites and Luminescence," Chem. Eur. J. 14(23):6978-6986, Aug. 8, 2008.
Uchiyama, M., et al., "Regiocontrolled Intramolecular Cyclizations of Carboxylic Acids to Carbon-Carbon Triple Bonds Promoted by Acid or Base Cataylst," Organic Letters 8(24):5517-5520, Nov. 23, 2006.

* cited by examiner

*Primary Examiner* — Nizal Chandrakumar
(74) *Attorney, Agent, or Firm* — Christensen O'Connor Johnson Kindness PLLC

(57) ABSTRACT

The present invention provides a compound having absorbing and luminescence wavelengths at relatively longer wavelength side of the visible area, and having thermal stability, which acts as a dye and/or a luminescence material and has practical utility therefor, and a production method thereof. The above subject of the present invention can be solved by a compound represented by general formula I: $R_1—X—R_2$, wherein $R_1$ and $R_2$ each independently represents, for example, an N,N-diaryl-4-aminophenyl group, and X is one condensed ring group selected from the group consisting of following formulae X-1 to X-3:

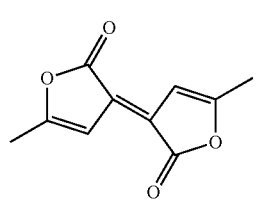

X-1

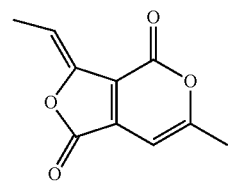

X-2

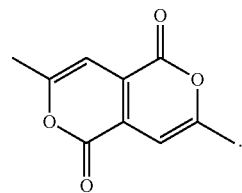

X-3

4 Claims, 3 Drawing Sheets

COMPOUND COMPRISING TRIARYLAMINE MOIETIES AND A CONDENSED RING MOIETY, AND THE PRODUCTION METHOD THEREOF

TECHNICAL FIELD

The present invention relates to a compound having a condensed ring moiety and mainly having triarylamine moieties, and a production method thereof. Further, the present invention relates to a dye and/or a luminescence material comprising the compound having the condensed ring moiety and mainly having the triarylamine moieties.

BACKGROUND ART

A part of the present inventors disclosed a diethynylethene derivative of a triarylamine-based molecule in Patent Document 1. It is disclosed that the derivative functions as a dye, a luminescence material, and a photochromic molecule.

Patent Document 1: WO 2009/098792.

DISCLOSURE OF INVENTION

Problem to be Solved by the Invention

However, the diethynylethene derivative of a triarylamine-based molecule disclosed in Patent Document 1 had a limitation that the absorption and luminescence wavelengths are at the shorter wavelength side of the visible area.

Further, the derivative had a problem that the thermal stability thereof is not relatively high.

Therefore, an object of the present invention is to provide a compound which does not cause the above-mentioned problems and a production method thereof.

More specifically, an object of the present invention is to provide a compound having absorbing and luminescence wavelengths at relatively longer wavelength side of the visible area, and having thermal stability, which acts as a dye and/or a luminescence material and has practical utility therefor, and a production method thereof.

Means for Solving Problems

The present inventors have earnestly studied in order to achieve the above-mentioned objects, and have found the following inventions:

<1> A compound represented by general formula I: $R_1$—X—$R_2$, wherein $R_1$ and $R_2$ each independently represents an N,N-diaryl-4-aminophenyl group, an N,N-diaryl-3-aminophenyl group, an N,N-diaryl-2-aminophenyl group, a 4-(carbazol-9-yl)phenyl group, a 3-(carbazol-9-yl)phenyl group, a 2-(carbazol-9-yl)phenyl group, or a derivative thereof, and X is one condensed ring group selected from the group consisting of following formulae X-1 to X-3:

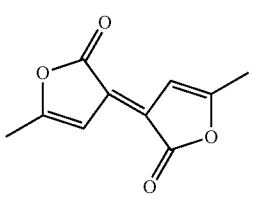

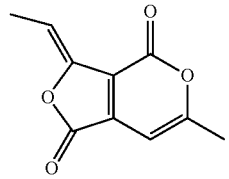

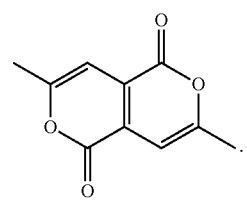

<2> In the above item <1>, $R_1$ and $R_2$ may be each independently an N,N-diaryl-4-aminophenyl group, an N,N-diaryl-3-aminophenyl group, an N,N-diaryl-2-aminophenyl group, or a derivative thereof, preferably an N,N-diaryl-4-aminophenyl group or a derivative thereof.

<3> In the above item <2>, the diaryl groups for $R_1$ and $R_2$ may be each independently one selected from the group consisting of i) an aryl group having 6 to 40 carbon atoms, ii) a heteroaryl group having 2 to 40 carbon atoms, iii) an aryl group having 6 to 40 carbon atoms which is substituted with one or more $R^3$ groups, and iv) a heteroaryl group having 2 to 40 carbon atoms which is substituted with one or more $R^4$ groups, wherein $R^3$ and $R^4$ groups are each independently selected from Group A consisting of a halogen atom; CN; $NO_2$; OH; $SiR^5R^6R^7$; $NR^8R^9$; $BR^{10}R^{11}$; a linear, branched or cyclic alkyl group having 1 to 40 carbon atoms; a linear, branched or cyclic alkoxy group having 1 to 40 carbon atoms; and a linear, branched or cyclic thioalkoxy group having 1 to 40 carbon atoms, wherein one or more non-adjacent carbon atoms may be substituted with —$CR^{12}$, =$CR^{13}$, $NR^{14}$—, —O—, —S—, —CO—O— or —O—CO—O—, and one or more H atoms may be replaced with fluorine, or selected from Group B consisting of i') an aryl group having 6 to 40 carbon atoms, ii') a heteroaryl group having 2 to 40 carbon atoms, iii') an aryl group having 6 to 40 carbon atoms which is substituted with one or more $R^{21}$ groups, and iv') a heteroaryl group having 2 to 40 carbon atoms which is substituted with one or more $R^{22}$ groups, wherein $R^{21}$ and $R^{22}$ groups are each independently a group selected from Group A, and the groups represented by $R^5$ to $R^{14}$ each independently represents a group selected from a hydrogen atom, and an aliphatic or aromatic hydrocarbon group having 1 to 20 carbon atoms.

<4> In any one of the above items <1> to <3>, the compound may be represented by any of following general formulae I-1 to I-3:
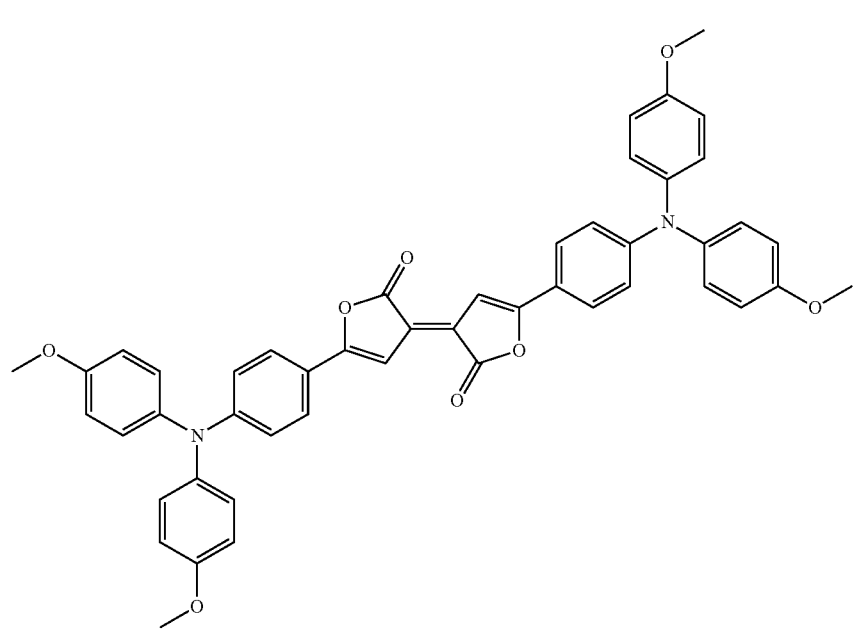
I-1
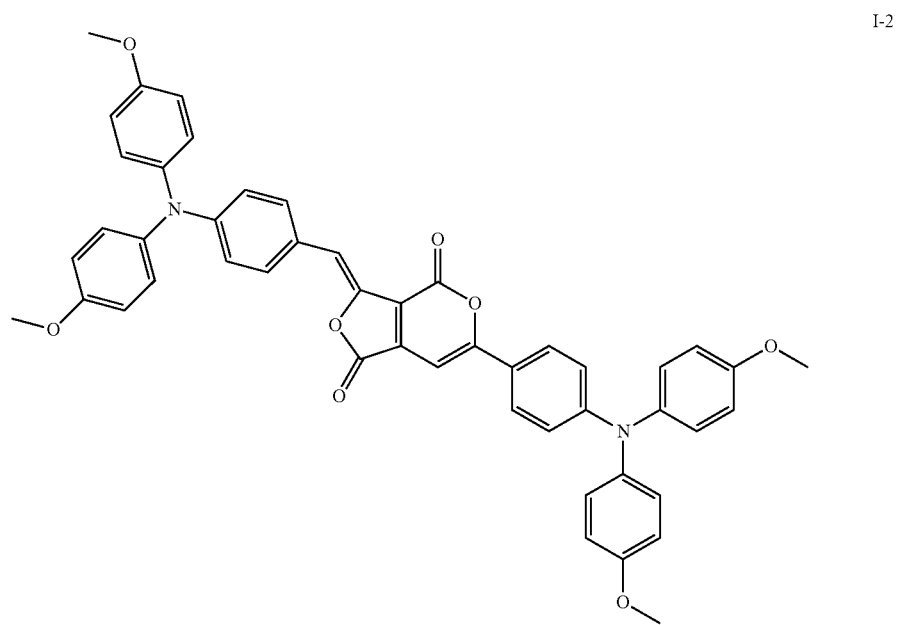
I-2

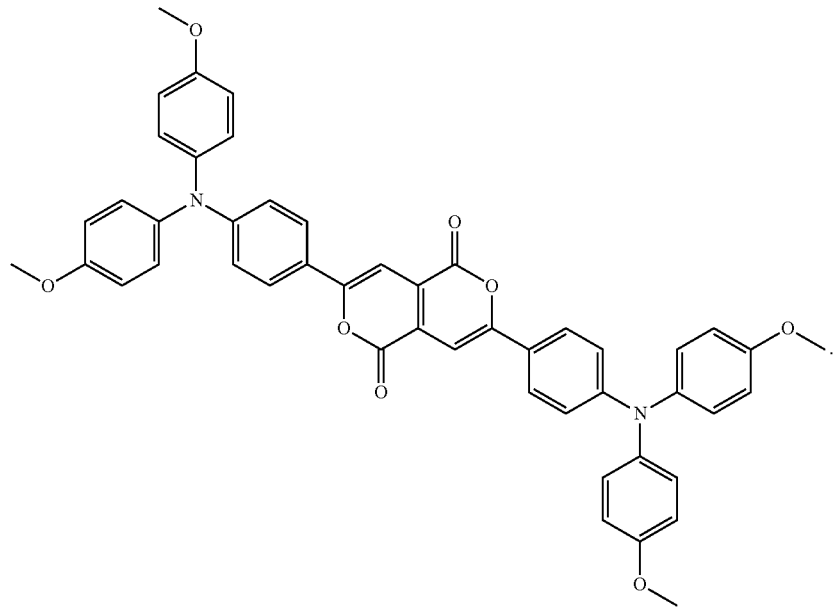

<5> A dye comprising the compound described in any one of the above items <1> to <4>.

<6> A luminescence material comprising the compound described in any one of the above items <1> to <4>.

<7> A method for producing a compound I represented by general formula I: $R_1$—X—$R_2$, wherein $R_1$ and $R_2$ each independently represents an N,N-diaryl-4-aminophenyl group, an N,N-diaryl-3-aminophenyl group, an N,N-diaryl-2-aminophenyl group, a 4-(carbazol-9-yl)phenyl group, a 3-(carbazol-9-yl)phenyl group, a 2-(carbazol-9-yl)phenyl group, or a derivative thereof, and X is one condensed ring group selected from the group consisting of following formulae X-1 to X-3, the method comprising the steps of:

A) preparing a compound II represented by formula II, wherein $R_1$ and $R_2$ each has the same definition as described above; and B) dissolving the compound II in an acid-resistant organic solvent, followed by adding an acid catalyst thereto, and heating the mixture or stirring the mixture under heating, to obtain the compound I:

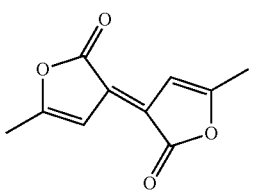
X-1

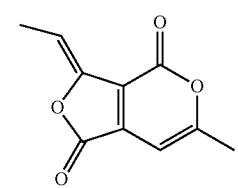
X-2

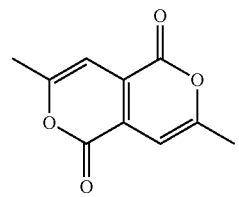
X-3

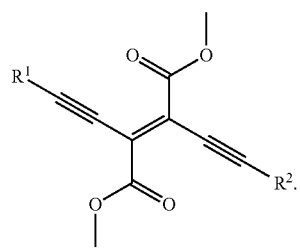
II

<8> In the above item <7>, $R_1$ and $R_2$ may be each independently an N,N-diaryl-4-aminophenyl group, an N,N-diaryl-3-aminophenyl group, an N,N-diaryl-2-aminophenyl group, or a derivative thereof, preferably an N,N-diaryl-4-aminophenyl group or a derivative thereof.

<9> In the above item <8>, the diaryl groups for $R_1$, and $R_2$ may be each independently one selected from the group consisting of i) an aryl group having 6 to 40 carbon atoms, ii) a heteroaryl group having 2 to 40 carbon atoms, iii) an aryl group having 6 to 40 carbon atoms which is substituted with one or more $R^3$ groups, and iv) a heteroaryl group having 2 to 40 carbon atoms which is substituted with one or more $R^4$ groups, wherein $R^3$ and $R^4$ groups are each independently selected from Group A consisting of a halogen atom; CN; $NO_2$; OH; $SiR^5R^6R^7$; $NR^8R^9$; $BR^{10}R^{11}$; a linear, branched or cyclic alkyl group having 1 to 40 carbon atoms; a linear, branched or cyclic alkoxy group having 1 to 40 carbon atoms; and a linear, branched or cyclic thioalkoxy group having 1 to 40 carbon atoms, wherein one or more non-adjacent carbon atoms may be substituted with —CR$^{12}$═, ═CR$^{13}$, NR$^{14}$—, —O—, —S—, —CO—O— or —O—CO—O—, and one or more H atoms may be replaced with fluorine, or selected from Group B consisting of i') an aryl group having 6 to 40 carbon atoms, ii') a heteroaryl group having 2 to 40 carbon atoms, iii') an aryl group having 6 to 40 carbon atoms which is substituted with one or more R$^{21}$ groups, and iv') a heteroaryl group having 2 to 40 carbon atoms which is substituted with one or more R$^{22}$ groups, wherein R$^{21}$ and R$^{22}$ groups are each independently a group selected from Group A, and the groups represented by R$^5$ to R$^{14}$ each independently represents a group selected from a hydrogen atom, and an aliphatic or aromatic hydrocarbon group having 1 to 20 carbon atoms.

<10> In any one of the above items <7> to <9>, the compound II may be represented by following formula II-1:

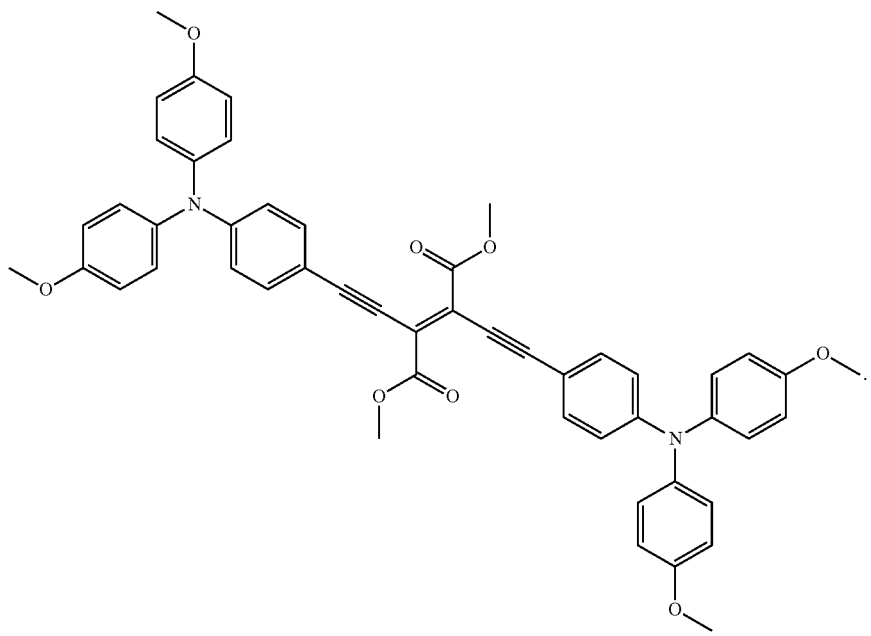

II-1

<11> In any one of the above items <7> to <10>, the compound I may be represented by any of the above formulae I-1 to I-3.

Effects of the Invention

The present invention can provide a compound having absorbing and luminescence wavelengths at relatively longer wavelength side of the visible area, and having thermal stability, which acts as a dye and/or a luminescence material and has practical utility therefor, and a production method thereof.

BEST MODE FOR CARRYING OUT THE INVENTION

Figure 1:
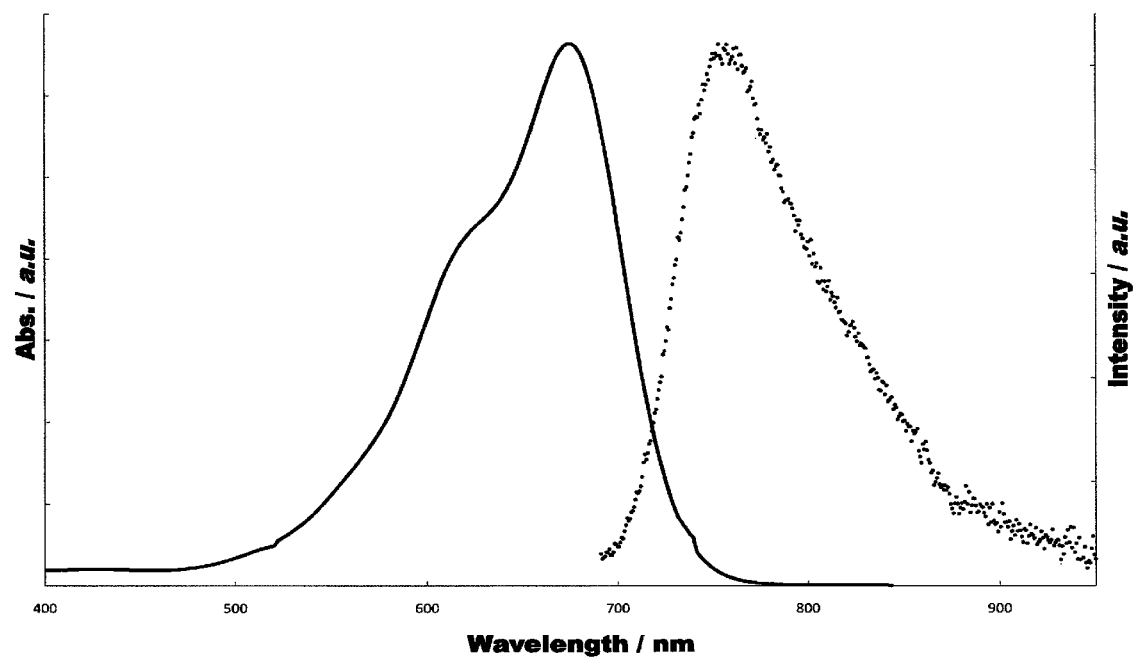
FIG. 1 is a drawing showing the absorption spectrum (solid line) and luminescence spectrum (dotted line) of a compound represented by formula I-1.

The present invention will be described in detail hereinafter.

The present invention provides a compound represented by general formula I: R$_1$—X—R$_2$.

In the formula, R$_1$ and R$_2$ each mainly represents a triarylamine moiety. More specifically, R$_1$ and R$_2$ each independently represents an N,N-diaryl-4-aminophenyl group, an N,N-diaryl-3-aminophenyl group, an N,N-diaryl-2-aminophenyl group, a 4-(carbazol-9-yl)phenyl group, a 3-(carbazol-9-yl)phenyl group, a 2-(carbazol-9-yl)phenyl group, or a derivative thereof.

Specifically, R$_1$ and R$_2$ each may independently represent an N,N-diaryl-4-aminophenyl group, an N,N-diaryl-3-aminophenyl group, an N,N-diaryl-2-aminophenyl group, or a derivative thereof, preferably an N,N-diaryl-4-aminophenyl group or a derivative thereof.

Further, the diaryl groups of R$_1$ and R$_2$ each may independently represent one selected from the group consisting of i) an aryl group having 6 to 40 carbon atoms, ii) a heteroaryl group having 2 to 40 carbon atoms, iii) an aryl group having 6 to 40 carbon atoms which is substituted with one or more R$^3$ groups, and iv) a heteroaryl group having 2 to 40 carbon atoms which is substituted with one or more R$^4$ groups, wherein R$^3$ and R$^4$ groups may be each independently selected from Group A consisting of a halogen atom; CN; NO$_2$; OH; SiR$^5$R$^6$R$^7$; NR$^8$R$^9$; BR$^{13}$R$^{11}$; a linear, branched or cyclic alkyl group having 1 to 40 carbon atoms; a linear, branched or cyclic alkoxy group having 1 to 40 carbon atoms; and a linear, branched or cyclic thioalkoxy group having 1 to 40 carbon atoms, wherein one or more non-adjacent carbon atoms may be substituted with —CR$^{12}$, =CR$^{13}$, NR$^{14}$—, —O—, —S—, —CO—O— or —O—CO—O—, and one or more H atoms may be replaced with fluorine, or selected from Group B consisting of i') an aryl group having 6 to 40 carbon atoms, ii') a heteroaryl group having 2 to 40 carbon atoms, iii') an aryl group having 6 to 40 carbon atoms which is substituted with one or more R$^{21}$ groups, and iv') a heteroaryl group having 2 to 40 carbon atoms which is substituted with one or more R$^{22}$ groups, wherein R$^{21}$ and R$^{22}$ groups are each independently a group selected from Group A, and the groups represented by R$^5$ to R$^{14}$ each may independently represent a group selected from a hydrogen atom, and an aliphatic or aromatic hydrocarbon group having 1 to 20 carbon atoms.

Further, X represents one condensed ring group selected from the group consisting of the groups represented by following formulae X-1 to X-3:

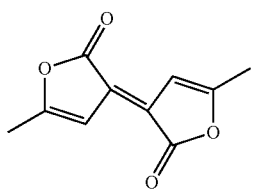

X-1

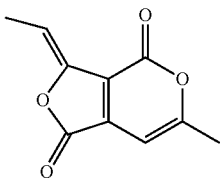

X-2

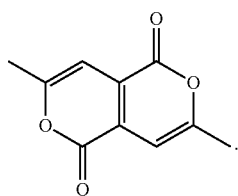

X-3

More specifically, the compound represented by the formula I may be any of following formulae I-1 to I-3.

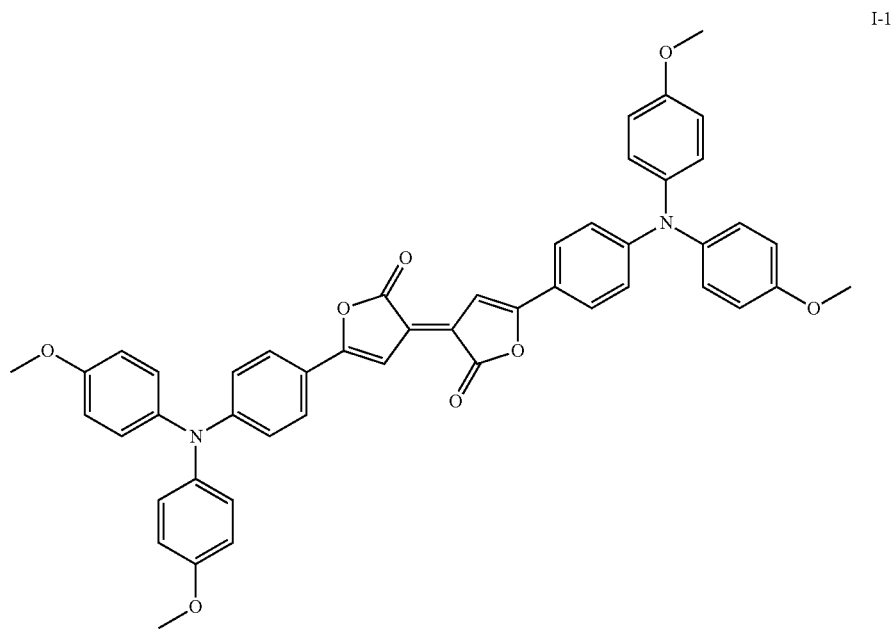

I-1

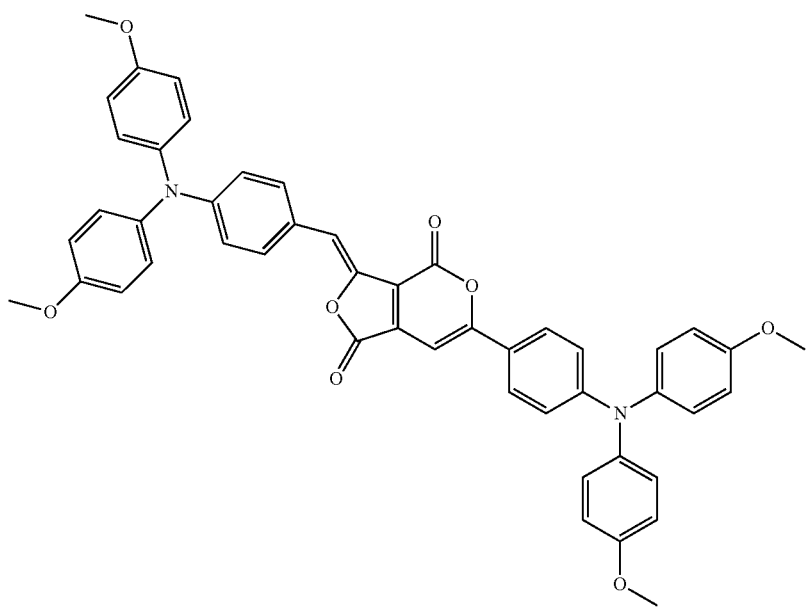

I-2

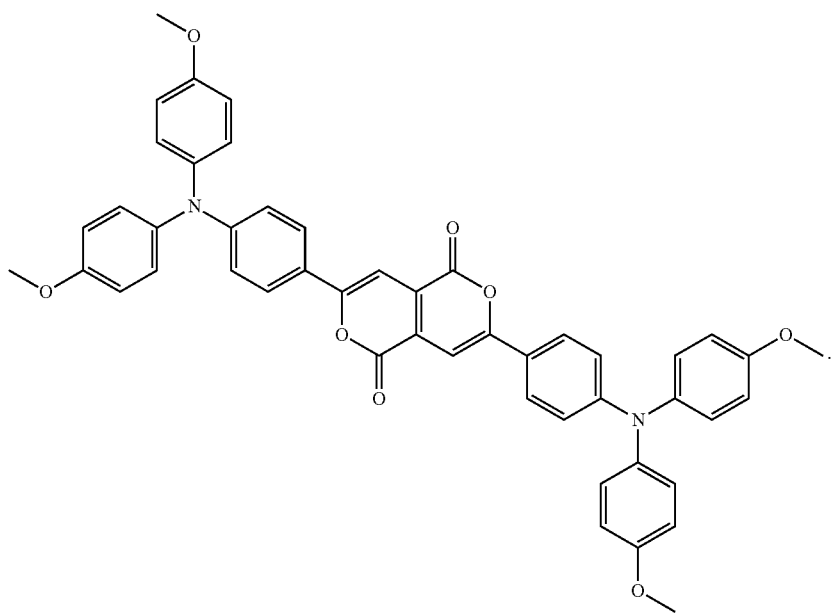

I-3

It is considered that a compound represented by general formula I according to the present invention which has the condensed ring moiety results in thermal stability.

Further, the compound represented by general formula I may have absorbing and luminescence wavelengths at relatively longer wavelength side in the visible area by strong electron donor/acceptor interaction generated by introducing a condensed ring in which a π-conjugate system is extended.

A compound represented by general formula I according to the present invention can provide a dye and/or a luminescence material consisting of the compound, and a dye and/or a luminescence material comprising the compound.

The compound represented by general formula I (hereinafter sometimes abbreviated as "compound I") can be produced, for example, by the following method.

The method comprises the steps of:

A) preparing a compound II represented by formula II, wherein $R_1$ and $R_2$ each has the same definition as described above; and B) dissolving the compound II in an acid-resistant organic solvent, followed by adding an acid catalyst thereto, and heating the mixture or stirring the mixture under heating, to obtain the compound I.

Furthermore, the compound I is the same as mentioned above.

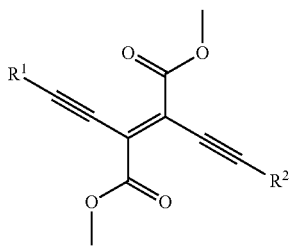

The step A) is a step in which the compound II is prepared. The compound II is the diethynylethene derivative described in Patent Document 1, i.e., WO2009/098792, and the derivative can be prepared according to the method disclosed in WO2009/098792. The whole content of WO2009/098792 is incorporated herein by reference.

The step B) is a step in which the compound II is dissolved in an acid-resistant organic solvent, an acid catalyst is added thereto, and the mixture is heated or stirred under heating.

Examples of the acid-resistant organic solvent may include carboxylic acids such as acetic acid, propionic acid, butyric acid and the like; and halogenated hydrocarbons, and preferable examples may include acetic acid, and halogen-based solvents such as dichloromethane, 1,2-dichloroethane, chloroform and carbon tetrachloride.

Examples of the acid catalyst may include inorganic acids such as hydrochloric acid, sulfuric acid and the like; organic acids such as tetrafluoroacetic acid, trifluoromethane sulfonamide and the like, preferably hydrochloric acid.

Further, the heating may be carried out, for example, at 40 to 200° C., preferably at about 100° C.

Furthermore, the compound II which is used as a raw material, depending on the objective compound I, may be, for example, represented be following formula II-1 when any of the formulae I-1 to I-3 is an objective compound:

The production method according to the present invention may comprise an additional step for purification after the step B). As the purification step, conventional methods such as chromatography may be used.

Hereinafter, the present invention will be illustrated with reference to Examples, but it is not to be construed as being limited thereto.

EXAMPLE 1

Synthesis of Compounds Represented by Formulae I-1 to I-3

The compounds represented by formulae I-1 to I-3 were synthesized as follows:

The compound II-1 was prepared according to the method disclosed in WO2009/098792.

The compound II-1 (500 mg, $6.35 \times 10^{-1}$ mmol) was dissolved in acetic acid (1000 ml) under nitrogen atmosphere, a small amount of hydrochloric acid (0.3 ml) was added thereto, and the mixture was stirred under heating at 100° C. for 24 hours.

The reactant was cooled, and pyridine (6 ml) was added thereto. Thereto, water and dichloromethane were added, to separate the liquid, and the dichloromethane layer was extracted. The solvent was distilled off under reduced pressure, and the residue was purified by silica gel column chromatography (eluent: dichloromethane) to give the compounds represented by the formulae I-1 to I-3.

Each of the resulting solids was recrystallized in a cold dark place at −30° C., by using toluene-hexane for the compound represented by the formula I-1 and dichloromethane-hexane for the compounds represented by the formulae I-2 and I-3, respectively.

The compounds represented by formulae I-1 to I-3 were identified by $^1$H-NMR as mentioned below, as well as by $^{13}$C-NMR, IR, MALDI-TOF-MASS and single-crystal X-ray structural analysis.

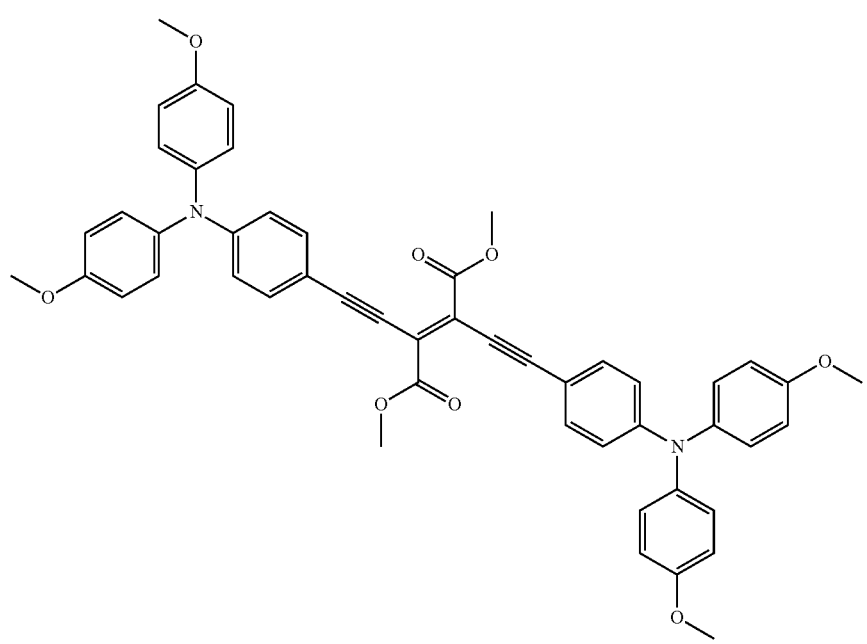

<NMR Data for Compounds Represented by Formulae I-1 to I-3>

<<Compound Represented by Formula I-1>>

$^1$H NMR (500 MHz, CDCl$_3$) δ=7.570 (4H, d, J=8.91), 7.329 (2H, s), 7.119 (8H, d, J=8.85), 6.92-6.88 (12H, m), 3.824 (12H, s).

<<Compound Represented by Formula I-2>>

$^1$H NMR (500 MHz, CDCl$_3$) δ=7.655 (4H, d, J=9.05), 7.13-7.10 (8H, m), 6.926 (1H, s), 6.90-6.86 (13H, m), 3.824 (6H, s), 3.818 (6H, s).

<<Compound Represented by Formula I-3>>

$^1$H NMR (500 MHz, CDCl$_3$) δ=7.645 (4H, d, J=8.21), 7.111 (8H, d, J=7.97), 7.106 (2H, s), 6.885 (4H, d, J=8.83), 6.880 (8H, d, J=8.81), 3.821 (12H, s).

<Absorption and Luminescence Spectra of Compounds Represented by Formulae I-1 to I-3>

The compounds represented by formulae I-1 to I-3 were each dissolved in toluene, and an absorption spectrum was measured using JASCO V570. Further, a luminescence spectrum was measured by dissolving each compound in toluene and using Hitachi F-4500 and an absolute quantum efficiency measurement apparatus.

Figure 2:
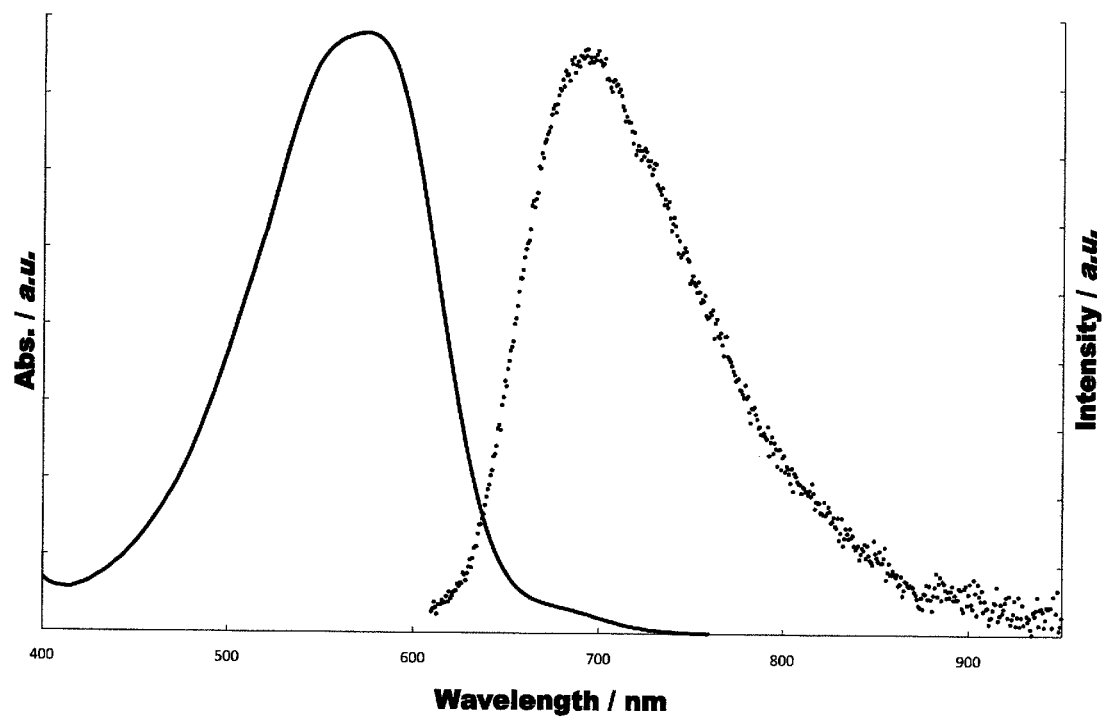
FIG. 2 is a drawing showing the absorption spectrum (solid line) and luminescence spectrum (dotted line) of a compound represented by formula I-2.
Figure 3:
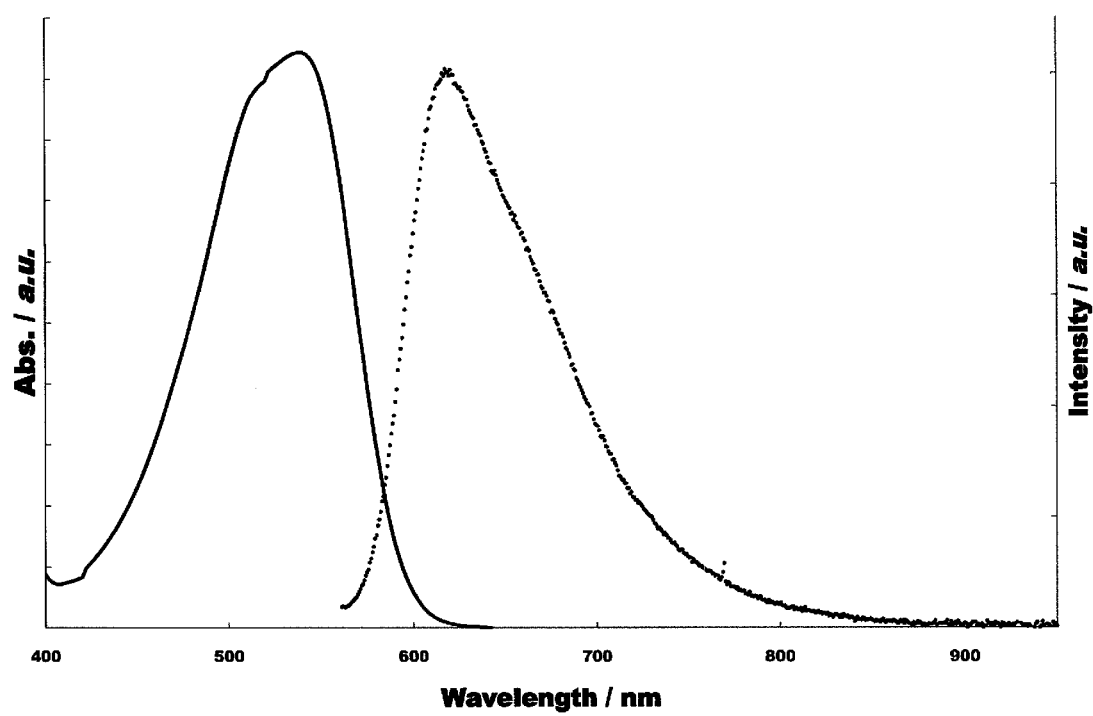
FIG. 3 is a drawing showing the absorption spectrum (solid line) and luminescence spectrum (dotted line) of a compound represented by formula I-3.

The results are shown in FIGS. 1 to 3.

FIG. 1 shows the absorption spectrum (solid line) and luminescence spectrum (dotted line) of the compound represented by formula I-1, FIG. 2 shows those of the compound represented by formula I-2, and FIG. 3 shows those of the compound represented by formula I-3.

FIG. 1 shows that the compound represented by formula I-1 has an absorption peak at 674 nm (molar distinction coefficient ε: 6.50×10$^4$ M$^{-1}$cm$^{-1}$) and a luminescence peak at about 750 nm (luminescence quantum efficiency φ: 0.27).

FIG. 2 shows that the compound represented by formula I-2 has an absorption peak at 574 nm (ε: 3.66×10$^4$ M$^{-1}$cm$^{-1}$) and a luminescence peak at about 700 nm (φ: 0.20).

FIG. 3 shows that the compound represented by formula I-3 has an absorption peak at 538 nm (ε: 5.00×10$^4$ M$^{-1}$cm$^{-1}$) and a luminescence peak at about 620 nm (φ: 0.82).

Furthermore, although not illustrated, the compound represented by formula II-1 has the following absorbing property and luminescence property, i.e., absorption peak: 482 nm; ε: 3.65×10$^4$ M$^{-1}$cm$^{-1}$; luminescence peak: 660 nm (φ: 0.15).

These results show that the absorption peaks of the compounds represented by formulae I-1 to I-3 are shifted to the longer wavelength side as compared to that of the compound represented by formula II-1. Further, the results show that the luminescence peaks of the compounds according to the present invention other than the compound represented by formula I-3 are also shifted to the longer wavelength side as compared to that of the compound represented by formula II-1. From them, it is confirmed that the compounds according to the present invention have improved practical utility.

<Results of Tg or DTA for Compounds Represented by Formulae I-1 and I-3>

The decomposition temperature was measured using a thermogravimetry analyzer apparatus (TGA) TA-Q500 type for the compounds represented by formulae I-1 and I-3, and found to be 348° C. and 402° C., respectively. Further, the glass transition temperature of the compound represented by formula II-1 was 186° C. These results show that the compounds represented by the formulae I-1 and I-3 has higher thermal stability than that of the compound represented by formula II-1. Also from them, it is confirmed that the compounds according to the present invention have improved practical utility.

What is claimed is:

1. A compound represented by general formula I: R$_1$—X—R$_2$, wherein R$_1$ and R$_2$ each represents an N,N-diaryl-4-aminophenyl group, or a 4-(carbazol-9-yl)phenyl group, X is one condensed ring group selected from the group consisting of following formulae X-1 to X-3:

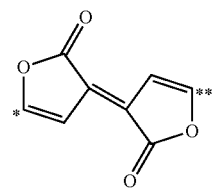

X-1

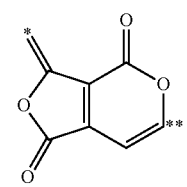

X-2

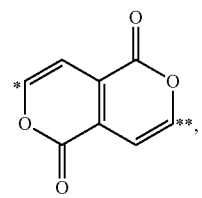

X-3 wherein R$_1$ is attached to a position * and R$_2$ is attached to a position **, and the diaryl groups for R$_1$ and R$_2$ are each independently selected from the group consisting of (i) an aryl group having 6 to 40 carbon atoms, (ii) a heteroaryl group having 2 to 40 carbon atoms, (iii) an aryl group having 6 to 40 carbon atoms which is substituted with one or more R$^3$ groups, and (iv) a heteroaryl group having 2 to 40 carbon atoms which is substituted with one or more R$^4$ groups, wherein R$^3$ and R$^4$ groups are each independently selected from Group A consisting of a halogen atom; CN; NO$_2$; OH; SiR$^5$R$^6$R$^7$; NR$^8$R$^9$; BR$^{10}$R$^{11}$; a linear, branched or cyclic alkyl group having 1 to 40 carbon atoms; a linear, branched or cyclic alkoxy group having 1 to 40 carbon atoms; and a linear, branched or cyclic thioalkoxy group having 1 to 40 carbon atoms, wherein one or more non-adjacent carbon atoms may be substituted with —CR$^{12}$, =CR$^{13}$, NR$^{14}$—, —O—, —S—, —CO—O— or —O—CO—O—, and one or more H atoms may be replaced with fluorine, or selected from Group B consisting of (i') an aryl group having 6 to 40 carbon atoms, (ii') a heteroaryl group having 2 to 40 carbon atoms, (iii') an aryl group having 6 to 40 carbon atoms which is substituted with one or more R$^{21}$ groups, and (iv') a heteroaryl group having 2 to 40 carbon atoms which is substituted with one or more R$^{22}$ groups, wherein R$^{21}$ and R$^{22}$ groups are each independently a group selected from Group A, and the groups represented by R$^5$ to R$^{14}$ each independently represents a group selected from a hydrogen atom, and an aliphatic or aromatic hydrocarbon group having 1 to 20 carbon atoms.

2. The compound according to claim 1, wherein the compound is represented by any of following general formulae I-1 to I-3:
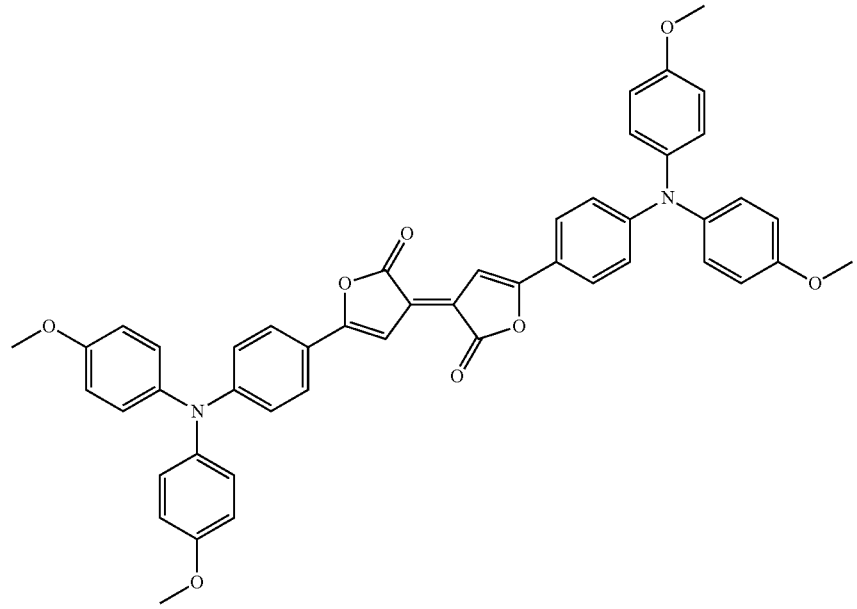
I-1
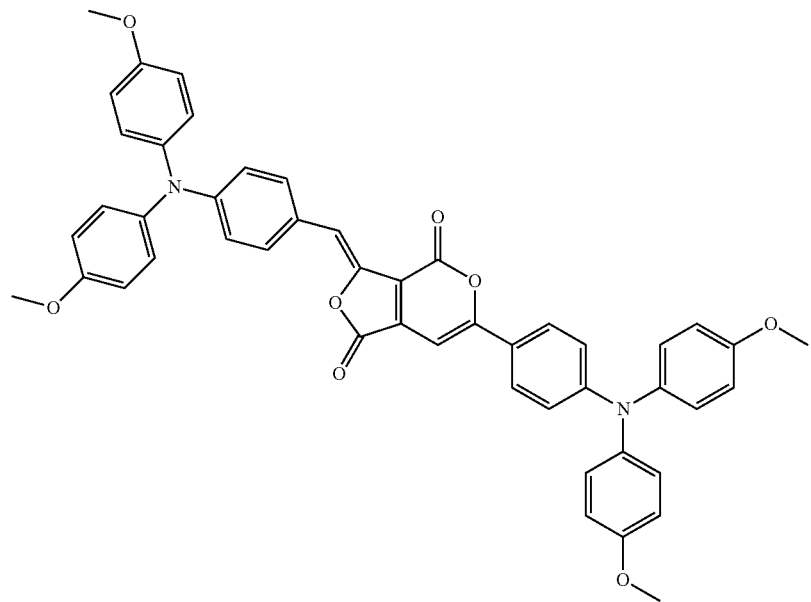
I-2

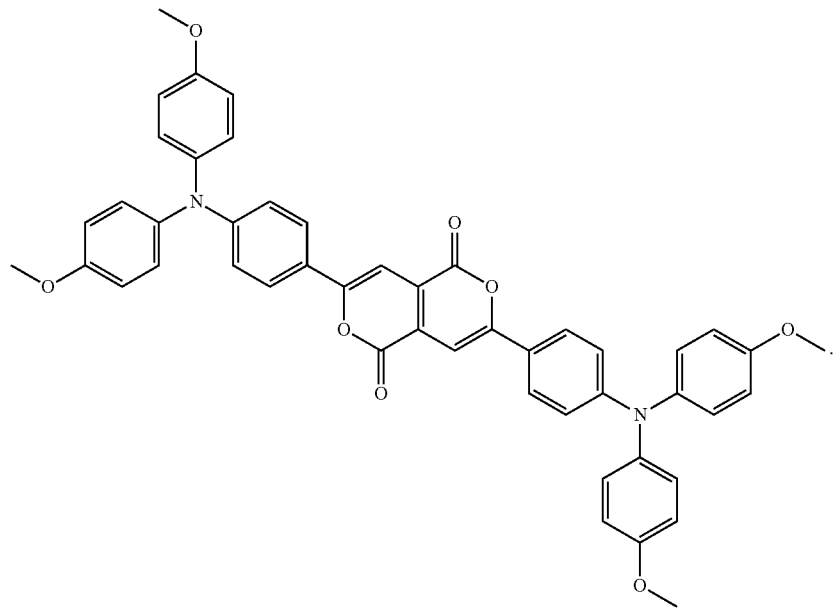
I-3
3. A dye comprising the compound according to claim 1.
4. A luminescence material comprising the compound according to claim 1.
* * * * *